United States Patent [19]

Leigh et al.

[11] Patent Number: 5,402,785

[45] Date of Patent: Apr. 4, 1995

[54] METHODS FOR MEASURING PERFUSION USING MAGNETIC RESONANCE IMAGING

[75] Inventors: John S. Leigh; John A. Detre, both of Philadelphia; Donald S. Williams; Alan P. Koretsky, both of Pittsburgh, all of Pa.

[73] Assignees: Trustees of the University of Penna, Philadelpha; Carnegie Mellon University, Pittsburgh, both of Pa.

[21] Appl. No.: 746,771

[22] Filed: Aug. 16, 1991

[51] Int. Cl.$^6$ ............................................. A61B 5/055
[52] U.S. Cl. .............................. 128/653.2; 128/653.3; 324/309
[58] Field of Search ............... 128/653.1, 653.2, 653.3, 128/653.4; 324/306, 307, 309

[56] References Cited

U.S. PATENT DOCUMENTS

| | | | |
|---|---|---|---|
| 4,445,515 | 5/1984 | Di Resta | 128/635 |
| 4,520,828 | 6/1985 | Burl et al. | 128/653.3 |
| 4,532,473 | 7/1985 | Wehrli | 128/653.3 |
| 4,602,641 | 7/1986 | Feinberg | 128/653.3 |
| 4,654,594 | 3/1987 | Seppnen | 324/309 |
| 4,669,481 | 6/1987 | Eisenberg et al. | 128/654 |
| 4,706,025 | 11/1987 | Edelstein et al. | 324/309 |
| 4,709,703 | 12/1987 | Lazarow et al. | 128/654 |
| 4,788,500 | 11/1988 | Patz et al. | 128/653.3 |
| 4,809,701 | 3/1989 | Le Bihan et al. | 128/653.2 |
| 4,819,648 | 4/1989 | Ko | 128/653.1 |
| 4,962,357 | 10/1990 | Sotak | 128/653.2 |
| 5,016,637 | 5/1991 | Koizumi et al. | 128/653.3 |
| 5,070,876 | 12/1991 | Wright | 324/306 |
| 5,092,335 | 3/1992 | Le Bihan | 128/653.2 |
| 5,154,603 | 10/1992 | Sepponen | 324/306 |
| 5,183,045 | 2/1993 | Takamura et al. | 128/653.2 |
| 5,186,924 | 2/1993 | Fishman | 128/653.4 |
| 5,233,991 | 8/1993 | Wright | 128/653.3 |
| 5,270,654 | 12/1993 | Feinberg et al. | 324/309 |

OTHER PUBLICATIONS

Dr. Le Bihan et al., "MRI of Intravoxel Incoherent Motions, Applications to Diffusion and Perfusion in Neurologic Disorders," Radiology vol. 161, pp. 401–407 (1986).

M. Sardashti et al., "Spin-Labelling Angiography of the Carotids by Presaturation and Simplified Adiabatic Conversion," Magnetic Resonance Medical vol. 15, pp. 192–200 (1990) (Sardashti).

W. T. Dixon et al., "Projection Angiograms Of Blood Labelled By Adiobatic Fast Passage", Magnetic Resonance Medical, vol. 3, pp. 454–462, (1986) (Dixon).

Primary Examiner—K. M. Pfaffle
Attorney, Agent, or Firm—Woodcock Washburn Kurtz Mackiewicz & Norris

[57] ABSTRACT

Methods for measuring the perfusion of fluid in a substance are shown to include subjecting the fluid to electromagnetic energy so as to cause a response related to the magnetization of the fluid before it enters the substance, performing magnetic resonance measurements on the substance to generate intensity information and processing the intensity information to determine perfusion. In one embodiment of the invention, perfusion is measured by labeling atoms in the fluid at a base point, generating a steady state in the substance by continuing to label atoms until the effect caused by labeled atoms perfusing in the substance, reaches a steady state, generating image information for the substance and processing the image information to determine perfusion. It is preferred to label atoms by applying magnetic resonance perturbation. In one embodiment the labeling of atoms involves saturating spins associated with the atoms. In an especially preferred embodiment labeling involves inverting spins associated with the atoms continuously by adiabatic fast passage. Such inversion is preferably achieved by applying a radio frequency field virtually continuously. The invention is particularly useful where the substance is tissue and wherein the fluid is blood. In such an embodiment, labeling involves labeling the hydrogen atoms of water contained in the blood. It is also preferred for labeling to occur at a point between the heart and the tissue. It is also especially preferred for the generation of magnetic resonance images to involve generating a first image while labeling at the base point, labeling at a remote point, generating a second image while labeling at the remote point and generating a relaxation image. In such an embodiment, all of the images are processed in the determination of perfusion.

21 Claims, 5 Drawing Sheets

METHODS FOR MEASURING PERFUSION USING MAGNETIC RESONANCE IMAGING

The research disclosed in this patent application was supported in part by the National Institutes of Health. The United States government has certain rights in the invention.

FIELD OF THE INVENTION

The present invention relates generally to the field of perfusion measurement and more particularly to methods for non-invasively measuring perfusion.

BACKGROUND OF THE INVENTION

Measurement of tissue perfusion, i.e. the flow of fluid in tissue, is important for the functional assessment of organs in vivo. Although the terms perfusion and flow are sometimes used interchangeably, perfusion as used herein refers to a diffusable exchange between a fluid and a substance. In relation to tissue, perfusion is tissue specific and refers to the exchange of oxygen, water or nutrients from blood to tissue.

A number of techniques have been developed to measure tissue perfusion in vivo and in vitro. For example, the wash-in or wash-out kinetics of exogenously administered tracers have been used to measure flow. With diffusible tracers, this type of measurement can yield tissue perfusion rates.

There are two basic classes of experiments used to determine perfusion with tracers: (a) measurement of the terminal deposition of a tracer and (b) measurement of a freely diffusible tracer either by wash-in/wash-out kinetics or by the determination of steady-state tissue level of the tracer. An example of a terminal deposition tracer is radiolabelled microspheres.

There are numerous diffusible tracers, detectable by a variety of techniques, which have been used to measure perfusion. These include Xenon, detected by radioactivity or CT scans, and $^{15}$O-water and $^{18}$F-fluoromethane, detected by positron-emission tomography. These techniques all rely on the administration of exogenous tracers, and may require arterial blood sampling for quantification.

Recently, there have been a number of applications of magnetic resonance imaging (MRI) techniques to measure tissue perfusion. MRI provides detailed images of the human body with soft tissue contrast not achievable with prior imaging techniques. Due to the versatility of this modality, non-invasive evaluations can be made of tissue anatomy, pathology, metabolism and flow.

Magnetic resonance (MR) is defined as the enhanced absorption of energy occurring when the nuclei of atoms or molecules within an external magnetic field are exposed to radio frequency (RF) energy at a specific frequency, called the Larmor or resonance frequency. Drs. Bloch and Purcell each received the Nobel Prize for investigating and describing in 1946 the phenomenon of MR in solids and liquids. The characteristics of the MR signal arising from a given nucleus were found to depend on a specific molecular environment of that nucleus and such signal dependence proved ideal for qualitative and quantitative chemical analysis. Moreover, the radio frequencies involved in MR are nonionizing and can penetrate the human body.

Although MR suggested enormous clinical potential for in vivo studies, the potential of the method was limited by its inability to provide spatial localization of the MR signal. Lauterbur resolved the localization problem through the use of magnetic field gradients. Since 1977, various MR techniques have been developed for the generation of two and three dimensional data of a human subject.

The production of an MR image can be summarized by the following steps. First, randomly oriented nuclei are aligned by a powerful uniform magnetic field. Second this alignment of magnetization is disrupted by properly tuned RF pulses. These pulses disrupt or perturb the nuclei alignment. As the nuclei recover their alignment by relaxation processes, they produce radio signals proportional to the magnitude of their initial alignment. Contrast between nuclei develops as a result of the different rates at which each nuclei realigns with the magnetic field. Third, the positions of the nuclei are localized by the application of a spatially dependent magnetic field called a gradient. Fourth, the radio signals produced by the realigning nuclei are measured or read out after a predetermined time has elapsed from the initial RF excitation. Fifth, the measured or read out signals are transformed by means of a Fourier Transform into data having a particular position in the image being generated. For a more complete discussion of MRI methods and equipment, see R. R. Edelman et al., Clinical Magnetic Resonance Imaging, W. B. Saunders (U.S.A.) (1990), which work is incorporated herein by reference.

Application of magnetic resonance imaging (MRI) techniques to measure tissue perfusion has in the past involved the determination of wash-in or wash-out kinetics of tracers such as $^2$H-water, $^{19}$F-trifluoromethane, and chelated gadolinium contrast agents. These experiments are analogous to those for detecting radiolabeled tracers and require the administration of exogenous agents.

Another class of MR measurements exist which is aimed at measuring volume fractions of endogenous tissue water. These methods offer the advantage of being entirely noninvasive and allow for unlimited serial measurements of blood flow. An example is the intravoxel incoherent motion (IVIM) imaging technique as described in D. Le Bihan et al., MRI of intravoxel incoherent motions: Applications to diffusion and perfusion in neurologic disorders, Radiology Vol. 161, p. 401–407 (1986), incorporated herein by reference. This technique attempts to generate perfusion contrast based on the microscopic diffusion of tissue water rather than on tracer kinetics. However, while IVIM yields interesting contrast in images, the exact relationship of the measured quantity by this technique to tissue perfusion rates is not yet clear.

Consequently, a need exists for methods which permit non-invasive measurement of perfusion without the need for the administration of exogenous agents and which provides significantly greater resolution than those methods presently employed.

The present invention involves an alternative technique for proton magnetic resonance imaging of perfusion rates using a fluid as a diffusible tracer. In the specific case of measuring brain prefusion, described below in Examples 1 and 2, the method involves labelling proton spins of inflowing water in the arterial blood using magnetic resonance. In the examples, continuous saturation or inversion is performed proximal to the tissue or organ of interest. Continuous inversion may be achieved using an adiabatic excitation. For imaging perfusion in the brain, spins are labelled in the neck region.

Techniques for adiabatically inverting nuclear spins in arterial blood were described in M. Sardashti et al, "Spin-Labelling Angiography of the Carotids by Pre-saturation and Simplified Adiabatic Conversion," Magnetic Resonance Medical, Vol. 15, pages 192–200 (1990) (Sardashti) and W. T. Dixon et al., Projection angiograms of blood labeled by adiobatic fast passage, Magnetic Resonance Medical, Vol. 3, pps. 454–462 (1986) (Dixon) which Sardashti and Dixon articles are incorporated herein by reference. In Sardashti, the authors utilize labelled blood in order to investigate intraluminal arterial abnormalities. Such labelling technique was not used in measuring perfusion according to the present invention.

SUMMARY OF THE INVENTION

The advantages of the invention are achieved in a method for measuring perfusion of a fluid such as blood into a substance such as tissue. The method of the invention includes subjecting the fluid to electromagnetic energy so as to cause a response related to the magnetization of the fluid before it enters the substance, performing magnetic resonance measurements on the substance to generate intensity information and processing the intensity information to determine perfusion. In one embodiment of the invention, perfusion is measured by labeling atoms in the fluid at a base point, generating a steady state in the substance by continuing to label atoms until the effect caused by labeled atoms perfusing in the substance reaches a steady state, generating image information for the substance, and processing the image information to determine perfusion. It is preferred to label atoms by applying magnetic resonance perturbation. In one embodiment the labeling of atoms involves saturating spins associated with the atoms. In an especially preferred embodiment labeling involves inverting spins associated with the atoms continuously by adiabatic fast passage. Such inversion is preferably achieved by applying a radio frequency field virtually continuously.

The invention is particularly useful where the substance is tissue and wherein the fluid is blood. In such an embodiment, labeling involves labeling the hydrogen atoms of water contained in the blood. It is also preferred for labeling to occur at a point between the heart and the tissue. It is also especially preferred for the generation of magnetic resonance images to involve generating a first image while labeling at the base point, labeling at a remote point, generating a second image while labeling at the remote point and generating a relaxation image. In such an embodiment, all of the images are processed in the determination of perfusion.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which:

FIG. 5 is a comparison of conventional magnetic resonance imaging and perfusion imaging of a rat brain subjected to a regional cold injury, wherein FIG. 5A is a conventional $T_2$ weighted image (TE=60 ms, TR=2 s) where the inured region shows up a hyperintensity due to a longer $T_2$, and wherein FIG. 5B is a perfusion image of the same slice, where the grey scale is from 0 to 6 ml g$^{-1}$ min$^{-1}$ and the injured region is dark due to low flow.

DETAILED DESCRIPTION OF THE PREFERRED EMBODIMENT

Figure 1:
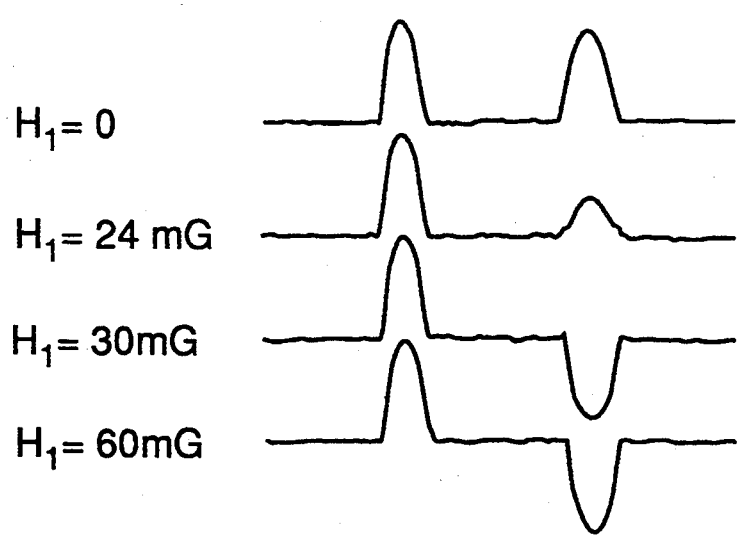
FIG. 1A is a graph depicting phantom studies on the effect of $H_1$ and velocity on spin inversion by adiabatic fast passage, wherein one-dimensional intensity profiles of a phantom consisting of stationary blood (left) and flowing blood (right), respectively, are shown as a function of radiofrequency field strength, $H_1$ used for inversion, where the blood is flowing through a gradient of 0.5 gauss cm$^{-1}$.
FIG. 1B is a graph of the degree of inversion in the phantoms in FIG. 1A of flowing blood as a function of flow velocity, wherein a gradient of 1.0 gauss cm$^{-1}$ and $H_1$ of 59 mgauss were used for all flow velocities.
Figure 1:
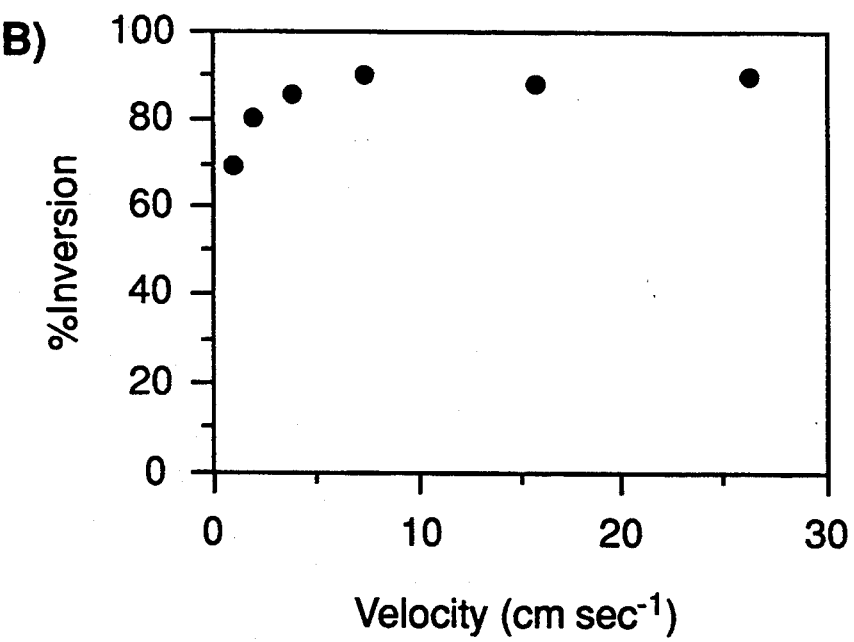

The method of the present invention is described below in relation to the determination of perfusion in the brain. The applicability and scope of the invention is not so limited. This method should also be useful in determining flow in any substance having a well defined fluid supply, e.g. any tissue having a well defined arterial supply such as kidney, liver and heart tissue. It would also be useful for magnetic resonance imaging of acute stroke and ischemia. However, all questions regarding the scope of the invention may be resolved by referring to the appended claims.

The inventive method involves proton magnetic resonance imaging of perfusion using water as a freely diffusable tracer. Application of the invention to the measurement of cerebral blood flow (CBF) in the rat is detailed in the examples.

Proximal labelling of blood flowing into the brain leads to a detectable effect on the brain $^1H$ image intensity. In other words, by continuously labelling blood at a location proximal to the flow of blood into the brain, e.g. in the neck, the effect of such labelling can be detected on the hydrogen nuclei of water molecules contained in the blood flow which have diffused into the brain. These hydrogen nuclei are used to generate a $^1H$ image intensity of brain tissue. The amount of change in a region of brain due to this effect depends on the blood flow to that region which delivers labelled spins and the regional $T_1$ which causes the magnetic resonance labelling to decay. A steady-state is thus created in which the intensity can be used to determine intravoxel values of blood flow.

Perfusion images can thus be generated via non-invasive techniques and without the need for exogeneous tracers. Additionally, determination of brain perfusion using the method of the present invention yields results in agreement with those results achievable using prior techniques. As will be described, labelling can be achieved by any magnetic perturbation which affect inflowing spins such as by saturation or optimally by spin inversion.

Generally, the method for determining perfusion involves labelling, i.e. perturbing, the proton spins of water present in the arterial blood by either saturation or inversion at a point upstream of the brain. The perturbed spins exchange with bulk water in the brain eventually reaching a steady state which exhibits a steady decreased intensity in a brain image. Spin inversion to label arterial blood water is preferably effected using principles of adiabatic rapid passage, as described by Sardashti et al. and Dixon.

The quantity of labeled blood in the brain is measured through its effect on the nuclear magnetization of water in the brain. In the presence of water flow into and out of the brain, the Bloch equations for brain water magnetization can be written as follows:

$$\frac{dM_b}{dt} = \frac{M_b^0 - M_b}{T_1} + fM_a - \frac{fM_b}{\lambda} \quad (1)$$

where, $f$ = brain perfusion in ml g$^{-1}$s$^{-1}$ $\lambda$ = brain blood partition coefficient for water defined as, $$\frac{\text{weight of water/g of brain}}{\text{weight of water/ml of blood}}$$

$T_1$ = Spin lattice relaxation time of brain water in the absence of flow or exchange between blood and brain $M_b$ = Z magnetization per gram of brain tissue (with proximal inversion)

$M_b^0$ = value of $M_b$ under fully relaxed conditions (without proximal inversion)

$M_a$ = Z magnetization per ml of arterial blood

In equation (1), $fM_a$ and $fM_b/\lambda$ represent the magnetization of the water entering and leaving the brain respectively. A well mixed compartment has been assumed such that the magnetization of spins leaving by venous flow has been replaced by the amount $fM_b/\lambda$. Under fully relaxed conditions, inflowing magnetization = outflowing magnetization thus, $$fM_a^0 = fM_b^0/\lambda \quad (2)$$

To simplify the solution to equation (1) in the case where arterial spins are inverted two assumptions are made. First is that all water spins in arterial blood entering the brain are inverted such that $M_a^0 = -M_a^0$. Second it is assumed that there is negligible relaxation of the inverted spins during the interval between inversion and exchange with brain spins so that $M_a = M_a^0$ at all times with these assumptions and equation (2) we can substitute $-fM_b^0/\lambda$ for $fM_a$ in equation (1) and then solve for $M_b$ to get, $$M_b(t) = \quad (3)$$

$$\frac{M_b^0}{1 + \frac{fT_1}{\lambda}} \left\{ \left(1 - \frac{fT_1}{\lambda}\right) + \frac{2fT_1}{\lambda} \exp-\left(\frac{1}{T_1} + \frac{f}{\lambda}\right) \right\}$$

Thus, continuous inversion of arterial spins results in an exponential decrease in $M_b$ with a time constant, $T_{1app}$ given by $$\frac{1}{T_{1app}} = \frac{1}{T_1} + \frac{f}{\lambda} \quad (4)$$

$T_{1app}$ is in and of itself dependent on blood flow. In the steady state, (=), $M_b$ reaches $M_b^{ss}$ given by, $$M_b^{ss} = M_b^0 \frac{\left(1 - \frac{fT_1}{\lambda}\right)}{\left(1 + \frac{fT_1}{\lambda}\right)} \quad (5)$$

From equations (3) and (4) it is easy to solve for the perfusion, f, which is given by, $$f = \frac{\lambda}{T_{1app}} \cdot \frac{M_b^0 - M_b^{ss}}{2M_b^{ss}} \quad (6)$$

$T_{1app}$, $M_b^0$, $M_b^{ss}$ and $\lambda$ are all measurable allowing f to be determined. In the case of saturation labelling, the relation would be:

$$f = \frac{\lambda}{T_{1app}} \cdot \frac{M_b^0 - M_b^{ss}}{M_b^{ss}} \quad (6a)$$

Spatially resolved perfusion maps may be obtained by carrying out the arterial spin inversion preceding an imaging sequence. For an arbitrary slice selection pulse with tip angle $\beta$ and assuming that the arterial spins in the slice are replenished with inverted spins fast compared to the TR interval, equation (1) can be solved to give the intensity ($M_b^{inv}$) on a pixel by pixel basis for an image acquired with arterial spin inversion described by, $$M_b^{inv}(TR) = \quad (7)$$

$$M_b^0 \frac{\left(1 - \frac{fT_1}{\lambda}\right)\left[1 - \exp-\left(\left(\frac{1}{T_1} + \frac{f}{\lambda}\right) \cdot TR\right)\right]}{\left(1 + \frac{fT_1}{\lambda}\right)\left[1 - \cos\beta \exp-\left(\left(\frac{1}{T_1} + \frac{f}{\lambda}\right) \cdot TR\right)\right]}$$

For a control image with no inversion, the image intensity, $M_b^{cont}$, is given by $$M_b^{cont} = M_b^0 \frac{\left[1 - \exp-\left(\left(\frac{1}{T_1} + \frac{f}{\lambda}\right) \cdot TR\right)\right]}{\left[1 - \cos\beta \exp-\left(\left(\frac{1}{T_1} + \frac{f}{\lambda}\right) \cdot TR\right)\right]} \quad (8)$$

solving equations (7) and (8) with, $$\frac{1}{T_{1app}} = \frac{1}{T_1} + \frac{f}{\lambda} \qquad (9)$$

yields $$f = \frac{\lambda}{T_{1app}} \frac{[M_b^{cont}(TR) - M_b^{inv}(TR)]}{2M_b^{cont}(TR)}$$

Equation (9) is identical to equation (6) in that a knowledge of the magnetization without inversion (control magnetization), the steady state magnetization with inversion of arterial spins, $T_{1app}$, and $\lambda$ gives CBF. The determination is independent of the tip angle, TR and other imaging parameters. Thus, a perfusion image can be generated from images with and without arterial spin inversion, and a $T_{1app}$ image.

The normal CBF for a rat brain is 1 ml.g$^{-1}$.min$^{-1}$, the $T_1$ (a reasonable estimate of $T_{1app}$) of the rat brain at 200 MHz is 1.7 s and $\lambda$ is 0.9 g.ml$^{-1}$ in brain tissue. Substitution of these values in equation (9) indicates that there should be a 6.4% fractional decrease in the intensity of a proton image of the brain with arterial spin inversion. While this is a relatively small change, it can be reliably detected because of the high sensitivity of proton MRI and because the measurement is made under steady-state conditions allowing time for signal averaging.

It will again be noted that the invention can be practiced using any perturbation which effects the magnetization of arterial water. The technique has been performed using saturation or inversion. Of these two, spin inversion is preferred because it maximizes the observed effect. In order to invert the arterial spins continuously, we make use of the technique described by Dixon and Sardashti el al. for inversion of moving spins. The method is based on the principles of Adiabatic Fast Passage (AFP) where inversion of spins can occur by the application of a continuous RF signal in the presence of a magnetic field that sweeps through resonance.

The conditions for AFP are, $$\frac{1}{T_1}, \frac{1}{T_2} << \frac{1}{H_1} \frac{dB_0}{dt} << \gamma H_1 \qquad (10)$$

where $H_1$, $B_0$, $\gamma$, $T_1$ and $T_2$ are the R.F. field strength, the magnetic field strength, the gyromagnetic ratio, the spin-lattice relaxation time and the spin-spin relaxation times, respectively. In the Dixon technique for the inversion of flowing spins, the R.F. signal is applied in the presence of a magnetic field gradient in the direction of the flow. In this way the movement of the spins through the magnetic field gradient leads to a change in magnetic field through resonance. The condition for AFP in this case is, $$\frac{1}{T_1}, \frac{1}{T_2} << \frac{1}{H_1} Gv << \gamma H_1 \qquad (11)$$

where G is the magnetic field gradient strength and v is the linear velocity of the flowing spins. Experimental values of G and $H_1$ can be easily chosen such that the above condition is satisfied For the examples given below, G=1.0 G cm$^{-1}$, $H_1$=59 mG, and v for blood in the rat carotid artery is approximately 10 cms$^{-1}$. These values give $\gamma H_1$=1571 rad s$^{-1}$ and Gv/$H_1$=170 s$^{-1}$.

Thus, the condition described by the right hand side of equation (10) is easily fulfilled with a large margin for possible changes in blood velocity in the arteries supplying the brain. Because 1/$T_2$ of blood in the rat (approximately 10 sec$^{-1}$) is larger than 1/$T_1$ of blood (approximately 0.59 sec$^{-1}$), $T_2$ is the parameter of concern to the conditions described by the left hand side of equation (11). However, for the parameters used in Example 2 below, this condition is satisfied as well.

EXAMPLE 1

$^1$H images were obtained with a Bruker 4.7 Tesla, 40 cm bore Biospec II imaging spectrometer operating at a proton frequency of 200 MH$_z$. A 15 cm diameter gradient insert capable of generating 12 gauss/cm with 50 μsec switching times was used. A 200-300 gm male Sprague-Dawley rat was isolated from physical vibrations caused by the imaging gradients by suspension on a board which was supported from outside the magnet. This was important for minimizing motion artifacts so that small regional changes in image intensity could be observed more reliably.

The rat head was placed in an 8 cm diameter $^1$H imaging coil. A 64×64 matrix spin echo imaging sequence was used, with TE=34 msec, TR=2 sec, slice thickness=2 mm, and FOV=50 mm, resulting in a pixel size of 0.8×0.8×2 mm. For $T_{1app}$ determinations the TR time was varied from 0.5 sec to 4 sec. Spin saturation during the TR period was performed using a series of slice selective (1 cm) 90° pulses, each followed by an x, y or z gradient homospoil pulse. Saturation was applied either proximal to the brain in the neck region, or to a control region outside the brain. Control or proximal saturation images consisting of two averages were alternated every four minutes. The saturation pulse and gradient was applied every 30 msec. In most experiments spoiler gradients were applied around the 180° pulse in the imaging sequence to eliminate signal from moving spins. These gradient pulses were adjusted to minimally attenuate diffusing spins (~4%), while eliminating faster moving spins (~99% for spins moving faster than 1 mm/sec).

Image processing was carried out on a MicroVAX computer using Interactive Data Language (IDL, Research Systems, Inc.). $T_{1app}$ maps were calculated from progressive saturation images by fitting each pixel to a monoexponential curve. Images were processed with a two point smoothing function, and interpolated to a 512 by 512 matrix. Two sets of control and proximal saturation images were summed for calculation of perfusion maps as described below, resulting in a total flow imaging time of sixteen minutes. Negative flow values were discarded.

A coronal image of the rat head and upper torso were obtained with proximal saturation. Signal intensity in the saturated slice (spaced forward of the rat head) was reduced to less than 5% of its non-saturated value by the saturation pulses. Perfusion measurements were made in a transverse slice equidistant between these two regions by alternating between control and proximal saturation. An image of this slice was obtained with control saturation. A difference image between control and proximal saturation was also obtained. This image showed the amount of saturated spins accumulated due to blood flow. Intensity in the region of the brain was clearly seen, and was significantly greater than the intensity in the surrounding muscle. The average intensity in the brain was 3.1% in the difference image as compared to the control image. This effect was not seen in a perfusion image made in accordance with the invention on a dead rat, indicating that the effect is dependent on blood flow.

However, a number of possible effects besides perfusion might contribute to the observed effect. Since proximal saturation affects intravascular spins which are not affected by the control saturation, the difference image could include a contribution from the arterial intravascular volume in addition to exchange of labeled vascular water with tissue water. Only the arterial vascular volume need be considered because essentially all water entering the brain exchanges with tissue water. To reduce this possible effect, symmetrical spoiler gradient pulses were used in the imaging sequence around the 180° pulse to eliminate intravascular signals in both proximal and control saturation images. Only 0.6% of total brain water is arterial, suggesting that even if the spoiler gradients had no effect the contribution of labeled arterial spins is small.

The method set forth above assumes that all the blood water is being saturated as it flows through the neck. To check this, the width of the slice which was being saturated was varied, increasing the time that flowing water would be in the saturation slice. No effect in the difference image was seen from 0.5 to 2.5 cm. A slice width of 1 cm was used, allowing a margin of error for complete saturation.

In addition, the method assumes that no relaxation of the saturated spins occurs until after they have exchanged with tissue water. If spins were relaxing significantly in the arteries before exchanging with tissue then the flow would be underestimated. Flow through the carotid artery of the rat at the level of the saturation slice is approximately 8 cm/sec (unpublished observation) and the distance from the edge of the saturation slice to the base of the brain was 0.5 cm. Therefore, it takes approximately 65 msec for saturated water in the blood to enter the brain arterial system. Rat brain blood flow is 1 $cc.gm^{-1}.min^{-1}$ through an intra-arterial volume of 0.6%, thus the longest time a spin spends in the brain arterial system is 360 msec. All together the saturated water takes a maximum of 425 msec to exchange with tissue water. At 4.7 Tesla the arterial blood water $T_1$ is 1.6 sec and the amount of relaxation which occurs can be calculated from $M_a/M_a^0 = 1-\exp(-\tau/T_1)$, with $\tau = 440$ msec and $T_1 = 1.6$ sec. Thus, at most spins relax 25% before exchanging with tissue water. Most of the saturated water in the blood will exchange in a significantly shorter time indicating that neglecting relaxation prior to exchange probably results in only a small underestimation of flow.

Recently, it has been reported that application of a saturation pulse up to 50 kHz from the water resonance in tissue leads to a large decrease in the $H_2O$ intensity. This is refered to as the Wolff-Balaban Effect. In the above images, the saturation slices are 15 kHz from the water in the perfusion detection slice, within the frequency range of the Wolff-Balaban effect. However, since the control slice is equidistant from the proximal saturation slice any such effect should cancel unless there is an asymmetrical Wolff-Balaban effect. To eliminate this possibility, the experiment was performed with the saturation slice selection gradient reversed, effectively switching the sides of the water resonance at which control and proximal saturation occur with respect to the detection slice. Similar results were obtained. In addition, no difference was seen in the dead brain, although a Wolff-Balaban effect should still be detected.

To measure perfusion in accordance with the present invention, images obtained with proximal and control saturation and a measurement of $T_{1app}$ are required. A $T_{1app}$ map of a rat brain was obtained in the transverse plane using the progressive saturation technique. The whole brain average from this slice was 1.71 sec in a normocapnic rat. This $T_1$ image was used in calculating perfusion maps, according to Eq. (9). The average $T_{1app}$ of whole brain measured in three rats was $1.58 \pm 0.09$ sec (mean±s.e.m.).

A perfusion map of the rat brain was obtained and displayed on a scale in units of cc.100 $g^{-1}.min^{-1}$. A published value of 0.9 cc/g for the partition coefficient of water was used (although a $\lambda$ map would provide more accurate quantification due to differing water contents of grey and white matter). The average CBF value over the whole brain was 106 cc.100 $g^{-1}.min^{-1}$. This value is in excellent agreement with the value for CBF in rat brain under halothane anesthesia of 105 cc.100 $g^{-1}.min^{-1}$ previously reported in the literature. This result is evidence that the assumptions of complete saturation of blood water and negligible relaxation of the spins until after exchange with tissue water which are used to quantitate perfusion are valid.

Individual pixel flow values ranged from 46 to 222 cc.100 $g^{-1}.min^{-1}$. Flow values are increased in the periphery of the brain, consistent with increased cortical flow. Small regions of very high flow seen bilaterally at the base of the brain may relate to the arterial supply (circle of Willis). Some intensity is also seen outside the brain, and is likely to be an artifact arising from the chemically shifted lipid signal. The mean global CBF under normocapnic conditions determined from three rats was $105 \pm 16$ cc.100 $g^{-1}.min^{-1}$ (mean±s.e.m.). To determine the sensitivity of this measurement to changes in CBF, flow images were made with hypercarbia. The arterial $pCO_2$ was increased to between 60 and 90 mm Hg in three rats and the mean global CBF rose to $227 \pm 18$ cc.$100g^{-1}.min^{-1}$.

The size of the perturbation of the tissue water due to proximal saturation of blood is small. It would be even smaller at the field strengths currently in use for human imaging, because $T_1$ is shorter at lower fields. One way to increase the effect would be to selectively invert the incoming spins rather than saturate them. This could be accomplished using an adiabatic fast passage induced by blood flowing through a field gradient with a constant RF field, as described above and shown in Example 2. As indicated above, this approach has been used to invert intravascular spins for MR angiography. Additional increases in signal to noise could be obtained by using quadrature or surface coil detection. Increased temporal resolution could be obtained by using an echo planar or other rapid imaging sequence to sample the Z magnetization after control or proximal saturation. Finally, interleaving of control and proximal saturation would reduce misregistration artifacts produced when these images are combined, particularly if the technique is applied to moving organs such as kidney or heart.

EXAMPLE 2

Animal Preparation

200–300 g male Sprague-Dawley rats were initially anesthetized with 5% halothane. After oral intubation, the rats were maintained on 1-2% halothane and a 1:1 $N_2O/O_2$ mixture using a Harvard rodent ventilator. A femoral arterial line was inserted to monitor blood pressure using a pressure transducer and chart recorder system and to sample blood gases which were analyzed on a Radiometer ABL2 blood gas machine. The core temperature of the rats was monitored with a rectal probe and maintained at 37±1° C. using a circulating water pad. Arterial $pCO_2$ was altered by adding varying amounts of $CO_2$ to the ventilator gas mixture. The mean arterial pressure was 100-120 mm Hg and typical control values for $pCO_2$ and $pO_2$ were 35 and 150 mmHg respectively. In the hypercarbia experiments, the $pCO_2$ levels were raised in a step wise fashion up to 100 mm Hg. Perfusion images were usually generated for control and two increased levels of $CO_2$ from each rat.

In the later part of this example, the rat brain was injured by freezing a localized region of the brain with a probe cooled with liquid nitrogen placed directly into the exposed skull for approximately 45 seconds. Sufficient time was allowed after freezing for the affected region to reach normal body temperature before imaging experiments were carried out. The nominal velocity of blood in the carotid artery of the rat was determined by measuring the velocity of blood in polyethylene tubing following catheterization with tubing of approximately the same internal diameter as the carotid artery.

MR Methods

Proton magnetic resonance images were obtained with a Biospec 4.7 Tesla 40 cm diameter MR spectrometer (Bruker Instruments, Billerica, Ma.) equipped with a 15 cm diameter gradient insert. The imaging probe used was a Bruker 7 cm diameter volume coil and image parameters were TR=2 s, TE=30 ms, FOV=5 cm, SLTH=2 mm and matrix size=64×64. The freeze-injured rat brain images were obtained with TR=2 s, SLTH=2 mm, FOV=5 cm and a 128×64 matrix resolution. The first two echoes (TE=30 and 60 msec) of a multi-echo imaging sequence were summed for the control and inversion images from the freeze-injured brain for improved S/N. The rats were isolated from the magnet by cantilevering them on a wooden beam from outside of the magnet so as to minimize the transition of physical vibrations from the gradient coils.

Inversion of the inflowing spins was effected using principles of adiabatic rapid passage as described by Sardashti et al., by applying a low power radio frequency field in the presence of a magnetic field gradient continuously during the TR period. The spatial location of the point of spin inversion was controlled by offsetting the frequency of the continuous r.f. It will be understood that the radio frequency field includes a center frequency. Therefore, control of the spatial location of the point of spin inversion can be achieved by offsetting the center frequency. Four pairs of images were obtained for each flow measurement with the inversion plane set alternately to the neck region (inversion image) and a plane outside the rat symmetrically opposite to the imaging detection plane (control image). The four images were summed for improved S/N. $T_{1app}$ values were measured using a saturation recovery imaging sequence with the arterial spins being continuously inverted during the recovery times of 10 s, 2 s, 1.5 s, 1 s and 0.5 s respectively. The r.f. power level and the gradient strength for the adiabatic fast passage were fixed at 0.059 gauss and 1.0 gauss $cm^{-1}$ respectively.

In order to ensure that these parameters are optimum for blood velocities found in the rat under physiological conditions, the degree of inversion was measured as a function of velocity, in a flow phantom of blood. The phantom consisted of a 2.25 mm diameter tygon tube. Oxygenated rabbit blood was infused through the tube at different rates with an infusion pump. For each flow rate, 1-D profiles of a 1 cm slice across the phantom were obtained at two frequencies of the continuous RF using a gradient echo sequence; (a) a control profile, where the frequency was set to resonance to a plane 1 cm downstream from the observed slice, and (b) an inversion profile, where the frequency is set to resonance to a plane 1 cm upstream from the observed slice. The degree of inversion, $\alpha$ was determined using the equation, $$M(\dagger)=M(0)[1-2\alpha \exp(-\dagger/T_1)]$$

where $\dagger$ is the time taken for the spins to travel from the inversion plane to the observation slice and, $M(\dagger)$ and $M(0)$ are the integrated areas of the profiles for the inversion and the control profiles respectively. $T_1$ and $T_2$ for the blood used in the phantom was measured using an inversion recovery sequence and a Hahn echo sequence respectively.

Image processing was carried out on the MR spectrometer's Aspect 3000 computer. $T_{1app}$ images were generated by a monoexponential fit of the saturation recovery image data at each pixel. Perfusion images were generated from the image data for the control image, inversion image, the $T_{1app}$ image, and a value of 0.9 g $ml^{-1}$ for $\lambda$ using equation (9).

FIG. 1A shows 1-D intensity profiles of a phantom consisting of a tube of blood flowing at 10 cm/sec and a tube of stationary blood as a function of the R.F. power level for the adiabatic inversion. The $T_1$ and $T_2$ of the blood in the phantom were 1.34 sec and 74 msec respectively, and the gradient for AFP was 0.5 gauss $cm^{-1}$. As the power levels for the adiabatic R.F. are increased spins in the flowing tube invert without any effect on stationary spins. Above a threshold power the inversion remains constant. In this case there was 90% inversion compared to the intensity when the R.F. was applied distal to the observation slice. The variation of the degree of inversion as a function of average velocity measured in the flow phantom is shown in FIG. 1B. For this experiment the R.F.power level and the gradient were fixed at 59 mgauss and 1 gauss $cm^{-1}$ respectively. There was 90% inversion over a range of flow velocities from 5 to 35 cm $sec^{-1}$. Below 5 cm $sec^{-1}$ the percent inversion began to fall off because of the left hand side of the AFP condition not being satisfied.

Figure 2:
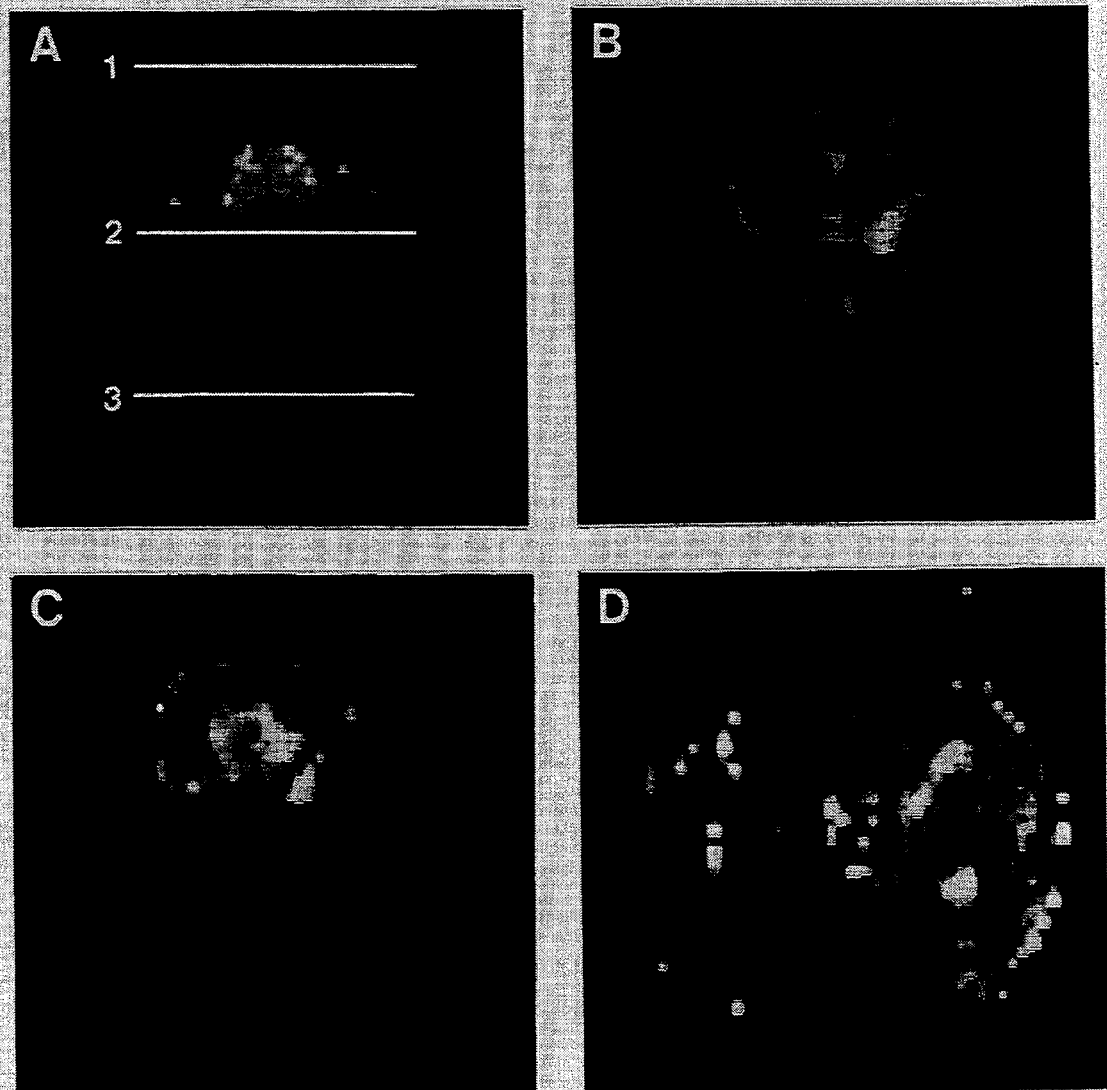
FIG. 2A is a coronal image of a rat head and upper torso, wherein the resonance planes for radiofrequency used for spin inversion by adiabatic fast passage for control and inversion images are indicated by 1 and 3, respectively, and plane 2 is the detection plane.
FIG. 2B is a control transverse image from the detection plane (plane 2 in 2A)
FIG. 2C is a difference image between control (2B) and inversion images (not shown)
FIG. 2D is a $T_{1app}$ image.

FIG. 2A shows a coronal image of a rat head and upper torso indicating the detection plane (2) used to quantitate perfusion, the resonance plane (3) and the control plane (1) for the adiabatic inversion R.F. for the inversion. The control transverse (axial) image is shown in FIG. 2B. FIG. 2C shows the difference image between control and inversion images for a rat under normocapnic conditions. Significant intensity is seen in the brain. This difference is not detectable from images from a dead rat (not shown), consistent with the idea that perfusion is being measured. These difference images only represent the accumulation of labelled spins due to perfusion, since actual perfusion is related quantitatively to the ratio of images. The excellent substraction in the case of the dead rat eliminates the possibility of substraction artifacts in these measurements. FIG. 2D shows a typical $T_{1app}$ image obtained from the rat brain and used in the calculation of the quantitative flow map. At 200 MHz $T_{1app}$ is rather uniform with a whole brain average of 1.6 sec and individual pixel values ranging from 1.2 sec to 2.1 sec.

Figure 3:
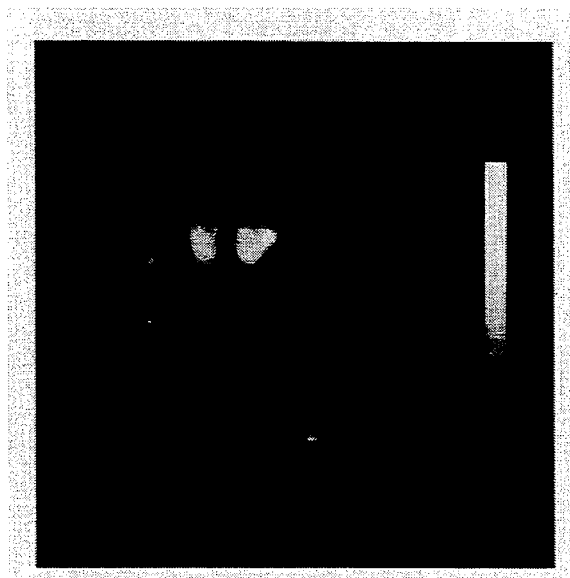
FIG. 3 is a perfusion image generated from data shown in FIG. 2, wherein the grey scale is from 0 to 8 ml m$^{-1}$ min$^{-1}$.

FIG. 3 shows a perfusion image obtained under condition of mild hypercapnia. A three point smoothing function has been applied to the image. The average whole brain perfusion rate is 3.0 ml.g$^{-1}$.min$^{-1}$ for this rat with moderate hypercapnia (pCO$_2$=60 mmHg). Regional flow rates vary from 1.7 to 6.7 ml.g$^{-1}$.min$^{-1}$. Increased flow rates are seen in the cortex and dead nuclei, while the dark regions of low flow occur in regions of the rat brain consisting of predominantly white matter. It is well established that white matter has lower perfusion rates than gray matter in mammalian brain.

Figure 4:
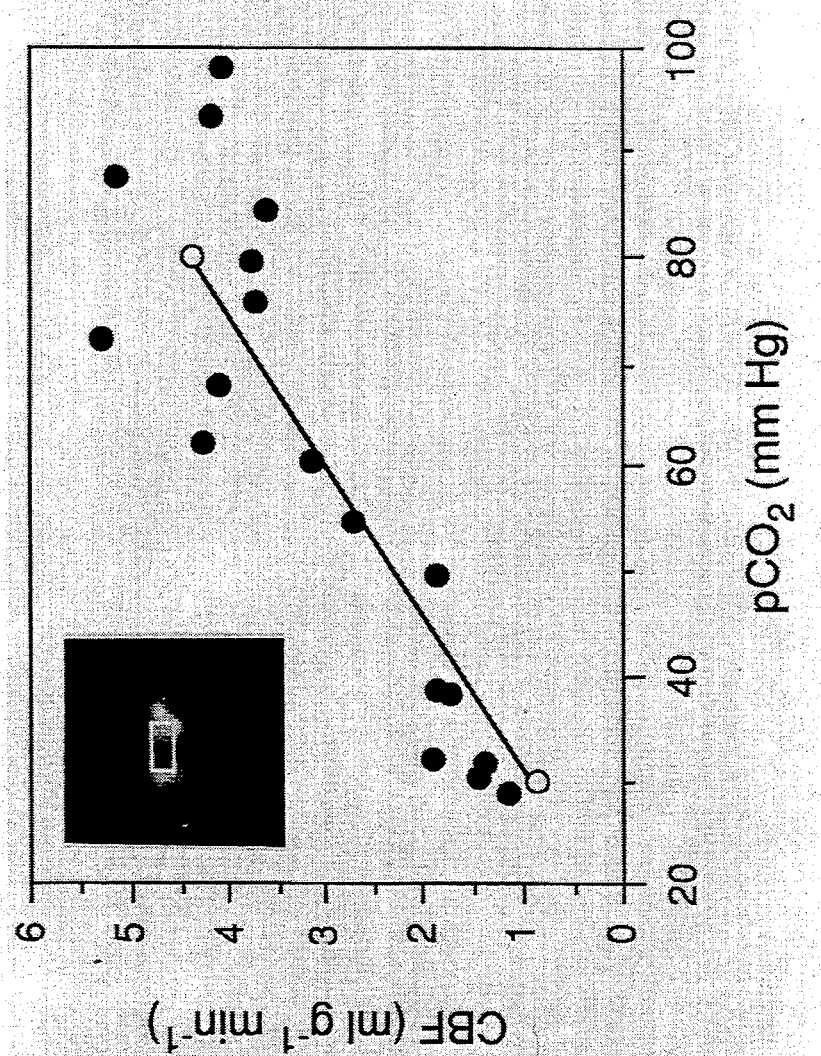
FIG. 4 is a graph of CBF to graded hypercarbia, wherein the region of the brain used to quantitate flow is indicated by a rectangle in the rat brain perfusion image shown in the inset, . is CBF measured by arterial spin inversion, ○ is published data which represents average whole brain blood flow determined using Xe as the CBF indicator and the solid line is derived from the published data.

For normocapnic rats (pCO$_2$=33±1.8 mm Hg), the average brain flow in the detection slice was 1.39±0.19 ml.g$^{-1}$.min$^{-1}$ (n=5). This value is in good agreement with previously reported literature values from 1 to 1.4 ml.g$^{-1}$.min$^{-1}$ for CBF in rat brain. The effects of graded hypercarbia on CBF from the deep nuclei of the brain is shown in FIG. 4. Hypercarbia increased flow in this region of the brain from a control flow of 1.6±0.14 ml.g$^{-1}$.min$^{-1}$ (mean±SEM, n=5) at a pCO$_2$ of 33±1.8 mm Hg (mean±SEM, n=5) to flows of 5.2 ml.g$^{-1}$.min$^{-1}$ at pCO$_2$ above 90 mm Hg. The solid line in FIG. 4 is derived from data from prior studies of the effects of graded hypercarbia on whole rat brain blood using Xenon washout techniques. This data gives a relation between CBF and pCO$_2$ up to 80 mm Hg defined by the equation CBG (ml.g$^{-1}$.min$^{-1}$)=0.07 pCO$_2$ (mm Hg)]−1.26. The data from this perfusion imaging determination of flow at pCO$_2$ up to 80 mm Hg yields a best-fit straight line described by CBF (ml.g$^{-1}$.min$^{-1}$)=0.052 [pCO$_2$(mm Hg)]−0.173. There is no significant difference (p>0.05) between the slopes of these two lines. This result shows that the MR perfusion imaging technique of the present invention yields values of CBF in excellent agreement with values obtained using established techniques and that the method of the present invention is sensitive to increases in perfusion due to hypercarbia.

Figure 5:
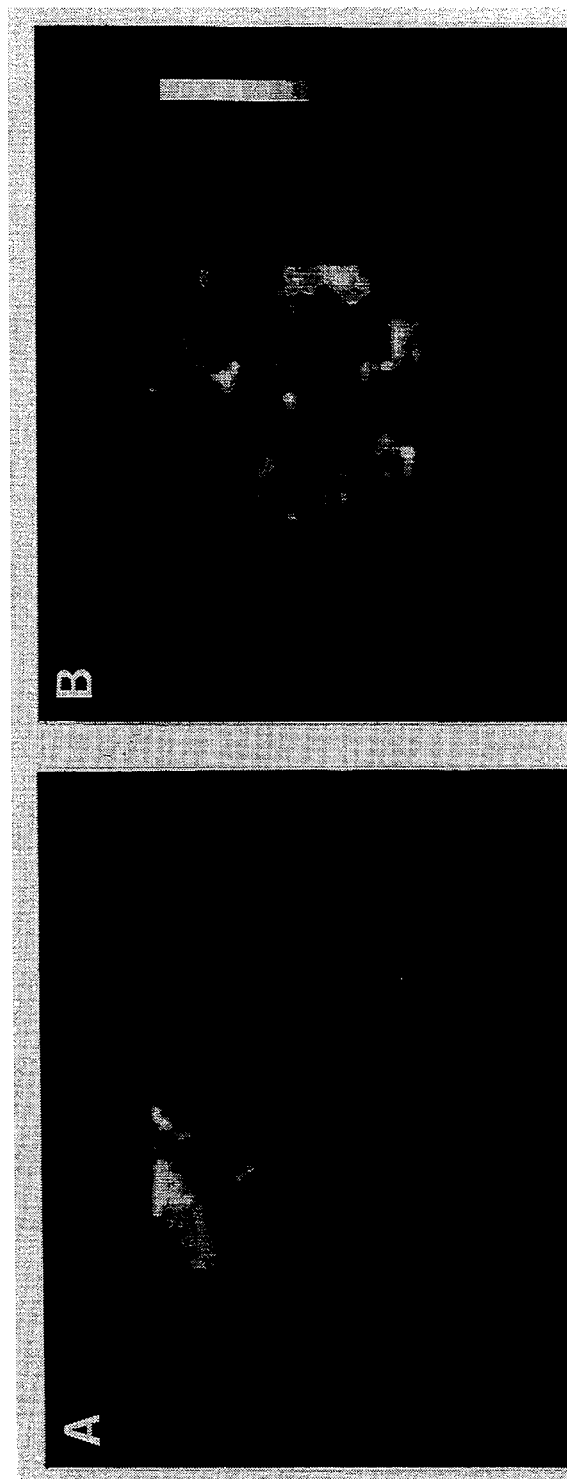

To assess the ability of the perfusion imaging technique to resolve abnormalities in flow, perfusion maps were obtained from a freeze-injured rat brain. Cryogenic lesions have been used to model focal cerebral injury and cause local edema formations and metabolic depression. FIG. 5A shows a normal $T_2$ weighted image of the rat brain after freeze-injury, where the affected region appears as bright semicircle in the upper left hand side of the image due to local edema. The $T_1$ also showed a slight increase in the injured region (data not shown). FIG. 5B shows the calculated flow image in the same slice. There is a region of low intensity corresponding to the injured region. These results show that the perfusion imaging technique is sensitive in detecting regional perturbations in blood flow. In this case, the perfusion image indicates a larger damaged region of the brain than does the conventional $T_2$ image.

The above described method involves labelling the arterial blood by spin magnetic resonance perturbation of its water protons at the neck region. By using adiabatic inversion (Example 2) of blood water spins, the invention, while being easier to implement, also gives a two fold improvement in S/N over the saturation technique (Example 1) allowing increased temporal or spatial resolution. Further, since the intraluminal spins are inverted rather than saturated, their intensity in the magnitude image is not affected as compared to the control inversion, and thus do not contribute intensity to the final flow image.

This approach to measuring tissue perfusion is appealing in that it is totally noninvasive, quantifiable, and yields flow images with the resolution of MRI. In principle, it can be applied to any organ with a well defined arterial supply including heart, liver and kidney, as well as brain. The application of this technique to human studies will require fast imaging methods to allow rapid interleaving of images obtained with and without inversion so that subtraction artifacts can be minimized. In addition, since the $T_1$ is field dependent, the technique will greatly benefit from the very high field systems currently coming into use. However, instances where blood flow in a specific volume is desired, the measurement can be made using volume localized spectroscopy with much higher S/N, and therefore lesser demands on field strength or motion reduction. This type of measurement could be easily combined with other volume localized spectroscopic techniques to provide information about blood flow and metabolism in a given region.

Besides perfusion, there are a number of other possible reasons that could explain the observed effect of reduction in the intensity of a proximal image under arterial spin inversion or saturation. A careful examination of these possible effects has been made to rule out the possibility of any artifacts contributing to our measurements.

While the invention has been described and illustrated with reference to specific embodiments, those skilled in the art will recognize that modification and variations may be made without departing from the principles of the invention as described herein above and set forth in the following claims.

What is claimed is:

1. A method for measuring the perfusion of fluid into a mass without requiring the use of an exogenous tracer and wherein the fluid passes a labelling position prior to perfusion into said mass, said method comprising the steps of:

magnetically labelling atoms in said fluid at said labelling position to produce labelled atoms;

allowing the labelled atoms in said fluid to perfuse into said mass;

generating image information, representing images with and without said labelled atoms, for the mass containing said fluid; and processing said image information to determine the quantity of said fluid per quantity of said mass per unit time which has perfused into said mass.

2. The method of claim 1, wherein the step of magnetically labelling atoms comprises the step of applying magnetic resonance perturbation to said labelling position.

3. The method of claim 2, wherein the step of magnetically labelling atoms comprises the step of saturating a spin associated with said atoms.

4. The method of claim 3, wherein the step of saturating a spin comprises the steps of applying a slice selective 90° pulse and applying a gradient homospoil pulse.

5. The method of claim 2, wherein the step of magnetically labelling atoms comprises the step of inverting spins associated with said atoms substantially continuously by adiabatic fast passage.

6. The method of claim 5, wherein the step of substantially continuously inverting spins comprises the step of repeatedly applying a radio frequency field.

7. The method of claim 6, wherein said radio frequency field comprises a center frequency and said step of generating image information comprises the step of controlling the spatial location of the point of spin inversion by offsetting said center frequency.

8. The method of claim 1, wherein said mass is tissue and said fluid is blood, and said step of magnetically labelling further comprises the step of labelling hydrogen atoms of water contained in said blood.

9. The method of claim 8, wherein said tissue is an organ and said step of labelling hydrogen atoms of water contained in said blood comprises the step of magnetically labelling at a labelling position between the heart and the organ so as to label water being carried from the heart to the organ.

10. The method of claim 9, wherein said organ is a brain and said step of magnetically labelling comprises the step of labelling the neck.

11. The method of claim 1, wherein said step of generating image information for said mass comprises the step of generating magnetic resonance images of said mass.

12. The method of claim 11, wherein said step of generating magnetic resonance images comprises the steps of generating a first image of said mass while said step of magnetically labelling at said labelling position is being performed, magnetically labelling at a location remote from said labelling position, generating a second image of said mass while said step of magnetically labelling at said remote location is being performed, and generating a relaxation image of said mass.

13. The method of claim 12, wherein said step of processing said image information comprises the step of processing the image information associated with said first and second images and said relaxation image.

14. The method of claim 13, wherein the step of processing the image information associated with said first and second images and said relaxation image comprises processing such information according to the formula:

$$f = \frac{\lambda}{T_{1app}} \frac{[M_b^{cont}(TR) - M_b^{inv}(TR)]}{\alpha M_b^{cont}(TR)},$$

where $M_b^{inv}$ is the image information associated with said first image, $M_b^{cont}$ is the image information associated with said second image, $T_{1app}$ is the image information associated with said relaxation image, $\alpha=2$ when said magnetically labelling step comprises the step of inverting spins associated with said atoms continuously by adiabatic fast passage and $\alpha=1$ when said magnetically labelling step comprises the step of saturating a spin associated with said atoms, and f is the quantity of said fluid per quantity of said mass per unit time which has perfused into said mass.

15. The method of claim 14, wherein said relaxation image comprises pixels and $T_{1app}$ is calculated from progressive saturation images by fitting each pixel of said relaxation image to a monoexponential curve.

16. The method of claim 14, wherein $T_{1app}$ is generated by applying a saturation recovery imaging sequence comprising a plurality of recovery times and spins which are continuously inverted.

17. The method of claim 1, further comprising the step of applying symmetrical spoiler gradient pulses during the step of generating image information.

18. The method of claim 1, wherein said step of generating image information comprises the steps of applying a multi-echo spin sequence to said mass, detecting two echoes and summing said echoes.

19. A method for measuring the perfusion of fluid into a mass, wherein the fluid passes a labelling position prior to perfusion into said mass, said method comprising the steps of:

magnetically labelling atoms in said fluid at said labelling position to produce labelled atoms;

allowing the labelled atoms in said fluid to perfuse into said mass;

generating image information representing images with said labelled atoms for the mass containing said fluid;

generating control image information representing images without said labelled atoms for the mass containing said fluid;

generating relaxation image information representing images of said mass; and processing said image information, control image information and relaxation image information to determine the quantity of said fluid per quantity of said mass per unit time which has perfused into said mass.

20. A method for measuring the perfusion of fluid into a mass without requiring the use of an exogenous tracer and wherein the fluid passes a labelling position prior to perfusion into said mass, said method comprising the steps of:

magnetically labelling atoms in said fluid at said labelling position to produce labelled atoms;

allowing the labelled atoms in said fluid to perfuse into said mass;

performing magnetic resonance measurements on said mass to generate intensity information for the mass containing said fluid; and processing said intensity information to determine the quantity of said fluid per quantity of said mass per unit time which has perfused into said mass.

21. The method of claim 20, wherein the step of magnetically labelling atoms comprises the step of inverting spins associated with said atoms substantially continuously by adiabatic fast passage, and wherein the quantity of said fluid per quantity of said mass per unit time which has perfused into said mass (f) is related to a time constant $T_{1app}$ representing the exponential decrease in the magnetization of said atoms per quantity of said mass by the equation:

$$\frac{1}{T_{1app}} = \frac{1}{T_1} + \frac{f}{\lambda},$$

where $T_1$ is a spin relaxation time for said atoms and $\lambda$ is a partition coefficient for water in said mass.

* * * * *

UNITED STATES PATENT AND TRADEMARK OFFICE
CERTIFICATE OF CORRECTION

PATENT NO. : 5,402,785

DATED : April 4, 1995

INVENTOR(S) : Leigh et al.

It is certified that error appears in the above-indentified patent and that said Letters Patent is hereby corrected as shown below:

Column 6, Line 17, "(=)" should read "($t=\infty$)"

Column 7, Line 19, "ml.g$^{-1}$.min$^{-1}$" should read "ml·g$^{-1}$·min$^{-1}$"

Column 7, Line 21, "g.ml$^{-1}$" should read "g·ml$^{-1}$"

Column 9, Line 41, "1 cc.gm$^{-1}$.min$^{-1}$" should read "1 cc·gm$^{-1}$·min$^{-1}$"

Column 10, Line 15, "cc.100 g$^{-1}$.min$^{-1}$" should read "cc·100 g$^{-1}$·min$^{-1}$"

Column 10, Line 20, "cc.100 g$^{-1}$.min$^{-1}$" should read "cc·100 g$^{-1}$·min$^{-1}$"

Column 10, Line 23, "cc.100 g$^{-1}$.min$^{-1}$" should read "cc·100 g$^{-1}$·min$^{-1}$"

Column 10, Line 29, "cc.100 g$^{-1}$.min$^{-1}$" should read "cc·100 g$^{-1}$·min$^{-1}$"

Column 10, Line 37, "cc.100 g$^{-1}$.min$^{-1}$" should read "cc·100 g$^{-1}$·min$^{-1}$"

Column 10, Line 42, "cc.100g$^{-1}$.min$^{-1}$" should read "cc·100g$^{-1}$·min$^{-1}$"

Column 11, Line 8, "C." should read "C"

Column 11, Line 38, "2 s" should read "2s"

Column 13, Line 10, "ml.g$^{-1}$.min$^{-1}$" should read "ml·g$^{-1}$·min$^{-1}$"

UNITED STATES PATENT AND TRADEMARK OFFICE
CERTIFICATE OF CORRECTION

PATENT NO. : 5,402,785
DATED : April 4, 1995
INVENTOR(S) : Leigh et al.

It is certified that error appears in the above-indentified patent and that said Letters Patent is hereby corrected as shown below:

Column 13, Line 12, "ml.g$^{-1}$.min$^{-1}$" should read "ml·g$^{-1}$·min$^{-1}$"

Column 13, Line 21, "ml.g$^{-1}$.min$^{-1}$" should read "ml·g$^{-1}$·min$^{-1}$"

Column 13, Line 23, "ml.g$^{-1}$.min$^{-1}$" should read "ml·g$^{-1}$·min$^{-1}$"

Column 13, Line 27, "ml.g$^{-1}$.min$^{-1}$" should read "ml·g$^{-1}$·min$^{-1}$"

Column 13, Line 29, "ml.g$^{-1}$.min$^{-1}$" should read "ml·g$^{-1}$·min$^{-1}$"

UNITED STATES PATENT AND TRADEMARK OFFICE
CERTIFICATE OF CORRECTION

PATENT NO. : 5,402,785
DATED : April 4, 1995
INVENTOR(S) : Leigh et al.

It is certified that error appears in the above-indentified patent and that said Letters Patent is hereby corrected as shown below:

Column 13, Line 34, "ml.g$^{-1}$.min$^{-1}$" should read "ml·g$^{-1}$·min$^{-1}$"

Column 13, Line 38, "ml.g$^{-1}$.min$^{-1}$" should read "ml·g$^{-1}$·min$^{-1}$"

Column 16, Line 18, ".atoms" should read "atoms"

Signed and Sealed this

Fourth Day of July, 1995

BRUCE LEHMAN

*Attest:*

*Attesting Officer*     *Commissioner of Patents and Trademarks*